(12) United States Patent
Johno et al.

(10) Patent No.: US 6,258,296 B1
(45) Date of Patent: Jul. 10, 2001

(54) FLUORINE-SUBSTITUTED COMPOUNDS AND FERRIELECTRIC LIQUID-CRYSTAL COMPOSITION CONTAINING THE SAME

(75) Inventors: Masahiro Johno; Yuki Motoyama; Takahiro Matsumoto, all of Katsushika-ku; Hiroshi Mineta, Chiyoda-ku; Tomoyuki Yui, Katsushika-ku, all of (JP)

(73) Assignee: Mitsubishi Gas Chemical Company INC, Tokyo (JP)

( * ) Notice: Subject to any disclaimer, the term of this patent is extended or adjusted under 35 U.S.C. 154(b) by 0 days.

(21) Appl. No.: 09/462,988

(22) PCT Filed: May 28, 1999

(86) PCT No.: PCT/JP99/02838

§ 371 Date: Jan. 19, 2000

§ 102(e) Date: Jan. 19, 2000

(87) PCT Pub. No.: WO99/62860

PCT Pub. Date: Dec. 9, 1999

(30) Foreign Application Priority Data

May 29, 1998 (JP) .................................. 10-149599
Jun. 26, 1998 (JP) .................................. 10-180898

(51) Int. Cl.$^7$ .......................... C09K 19/20; C09K 19/12; C07C 69/86; G02F 1/133

(52) U.S. Cl. ............................... 252/299.64; 252/299.65; 252/299.67; 560/62; 560/65; 560/83; 349/42; 349/43; 349/49; 349/50

(58) Field of Search .................. 252/299.64, 299.65, 252/299.66, 299.67; 428/1.1; 349/42, 43, 49, 50; 560/62, 65, 83

(56) References Cited

U.S. PATENT DOCUMENTS 6,001,278 * 12/1999 Matsumoto et al. ............ 252/299.65

FOREIGN PATENT DOCUMENTS 5150257   6/1993   (JP) .
5249502   9/1993   (JP) .

(List continued on next page.)

OTHER PUBLICATIONS

Keiichi Nito, et al., TFT–driven Monostable Ferroelectric Liquid Crystal Display . . . , SID '94, Preprint.

(List continued on next page.)

Primary Examiner—Shean C. Wu

(57) ABSTRACT

A fluorine-substituted compound of the following general formula (1) or (2), and a ferrielectric liquid crystal composition comprising the above compound and a specific ferrielectric liquid crystal compound,

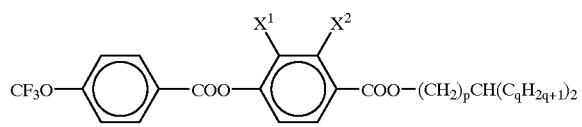

(1)

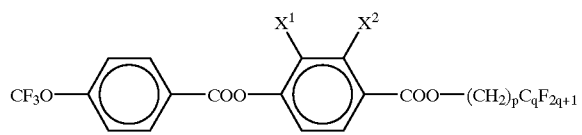

(2)

wherein, in the formula (1), each of $X^1$ and $X^2$ is a hydrogen atom, or one of them is a hydrogen atom and the other is a fluorine atom, p is an integer of 0 to 3 and q is an integer of 1 to 3, and in the formula (2), each of $X^1$ and $x^2$ is a hydrogen atom, or one of them is a hydrogen atom and the other is a fluorine atom, p is an integer of 1 to 3 and q is an integer of 1 to 3.

16 Claims, 1 Drawing Sheet

FOREIGN PATENT DOCUMENTS

| | | |
|---|---|---|
| 695080 | 4/1994 | (JP) . |
| 882778 | 3/1996 | (JP) . |
| 8127777 | 5/1996 | (JP) . |
| 8337555 | 12/1996 | (JP) . |
| 10330321 | 12/1998 | (JP) . |

OTHER PUBLICATIONS

Ewa Gorecka, et al., Molecular Orientational Structures . . . , Japanese Journal of Applied Physics, vol. 29, pp. 131–137, 1990.

Jurg Funfschilling, et al., Physics and Electronic Model . . . , Jpn. J. Appl. Phys., vol. 33, pp. 4950–4959, 1994.

Nobuhiro Okabe, et al., Reentrant Antiferroelectric Phase . . . , Jpn. J. Appl. Phys., vol. 31, pp. 793–796, Part 2, No. 6B, 1992.

* cited by examiner

FLUORINE-SUBSTITUTED COMPOUNDS AND FERRIELECTRIC LIQUID-CRYSTAL COMPOSITION CONTAINING THE SAME

CROSS-REFERENCE TO RELATED APPLICATION

This application is the National Phase entry, 35 USC 371, of International PCT application, PCT/JP99/02838, filed May 28, 1999, and designating the United States.

DETAILED DESCRIPTION OF THE INVENTION

1. Field of the Invention

The present invention relates to a novel fluorine compound and a ferrielectric liquid crystal composition containing the same. The ferrielectric liquid crystal composition of the present invention has small spontaneous polarization and has excellent response characteristics so that a ferrielectric liquid crystal display device having high display qualities can be materialized.

2. Prior Art

A liquid crystal display device (LCD) has been being widely used as a flat panel display as a substitute for a conventional Braun tube display (CRT), mainly in portable machines and equipment. Along with the recent expansion of the functions of personal computers and word processors and with the recent increase in the capacity of data processing, LCD is also required to have higher functions, that is, to have functions such as a large display capacity, a full-color display, a wide viewing angle, a high-speed response and a high contrast.

As a liquid crystal display method (liquid crystal driving method) to comply with such requirements, there has been proposed and is practically used an active matrix (AM) display device which works by a method in which thin film transistors (TFT) or diodes (MIM) are formed such that one transistor or diode corresponds to one pixel on a display screen and a liquid crystal is driven for one pixel independently of another.

Although the above display method has problems that it is difficult to decrease a cost due to a low production yield and that it is difficult to form a large-sized display screen, the above display method is about to surpass an STN display method which has been so far a mainstream and to overtake CRT due to its high display quality.

PROBLEMS TO BE SOLVED BY THE INVENTION

However, the above AM display device has the following problems due to the use of a TN (twisted nematic) liquid crystal as a liquid crystal material.

(1) A TN liquid crystal is a nematic liquid crystal, and the response speed is generally low (several tens ms), so that no good image quality can be obtained in the display of video rate.

(2) Since a twisted state (twist alignment) of liquid crystal molecules is used for displaying, the viewing angle is narrow. In displaying with a gray scale in particular, the viewing angle becomes sharply narrowed. That is, the contrast ratio, the color or the like changes depending upon viewing angles to a display screen.

For overcoming the above problems, there have been proposed AM panels which use a ferroelectric liquid crystal or an anti-ferroelectric liquid crystal in place of the TN liquid crystal (Japanese Laid-open Patent Publications Nos. 5-249502, 5-150257 and 6-95080). At present, however, the following problems remain to solve for the practical use of these liquid crystals.

(A) A ferroelectric liquid crystal has spontaneous polarization. An image sticking is liable to occur due to constant presence of the spontaneous polarization, and the driving is hence made difficult. In displaying with a ferroelectric liquid crystal, it is very difficult to perform a gray-scale display since only a binary display of black and white is possible in principle.

For the gray-scale display, a special artifice is required (for example, use of a ferroelectric liquid crystal device using monostability; Keiichi NITO et al., SID '94, Preprint, p. 48), and it is required to develop a high technique for practical use.

(B) An anti-ferroelectric liquid crystal is free from the image sticking problem described in the above (A) since it has no permanent spontaneous polarization.

In the AM driving, however, there is at least needed a liquid crystal material which can be driven at 10 V or lower. However, the anti-ferroelectric liquid crystal generally shows a high threshold voltage, and its driving at a low voltage is therefore difficult. Further, it has another problem that the gray-scale display is difficult to perform since its optical response involves a hysteresis.

It is an object of the present invention to provide a novel material that can overcome the above problems and is suitable for use in AM driving.

A ferrielectric liquid crystal is thinkable as the above novel material.

In 1989, a ferroelectric phase (SCγ* phase) was found for the first time in 4-(1-methylheptyloxy-carbonyl)phenyl-4-(4'-octyloxybiphenyl)carboxylate (called "MHPOBC" for short) that is an anti-ferroelectric liquid crystal compound (Japanese Journal of Applied Physics, Vol. 29, No. 1, pp. L131–137 (1990)).

The chemical structural formula and phase transition temperatures (° C.) of the MHPOBC are shown below.

Structural Formula:

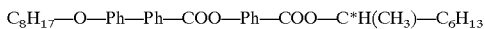

$C_8H_{17}$—O—Ph—Ph—COO—Ph—COO—C*H(CH$_3$)—C$_6$H$_{13}$ wherein Ph is a 1,4-phenylene group and C* is an asymmetric carbon.

Phase Sequence:

Cr(30)SIA*(65)SCA*(118)SCγ*(119)SC*(121)SCα*(122)SA(147)I wherein Cr is a crystal phase, SIA* is a chiral smectic IA phase, SCA* is a chiral smectic CA phase (anti-ferroelectric phase), SCγ* is a chiral smectic Cγ phase (ferrielectric phase), SC* is a chiral smectic C phase (ferroelectric phase), SCα* is a chiral smectic Cα phase, SA is a smectic A phase, and I is an isotropic phase.

Showing molecular arrangement states of a ferrielectric phase.

FI(+) and FI(−) show a ferrielectric state, and FO(+) and FO(−) show a ferroelectric state.

FIG. 2

Showing an optical response of a ferrielectric phase to a triangular wave voltage.

Figure 1:
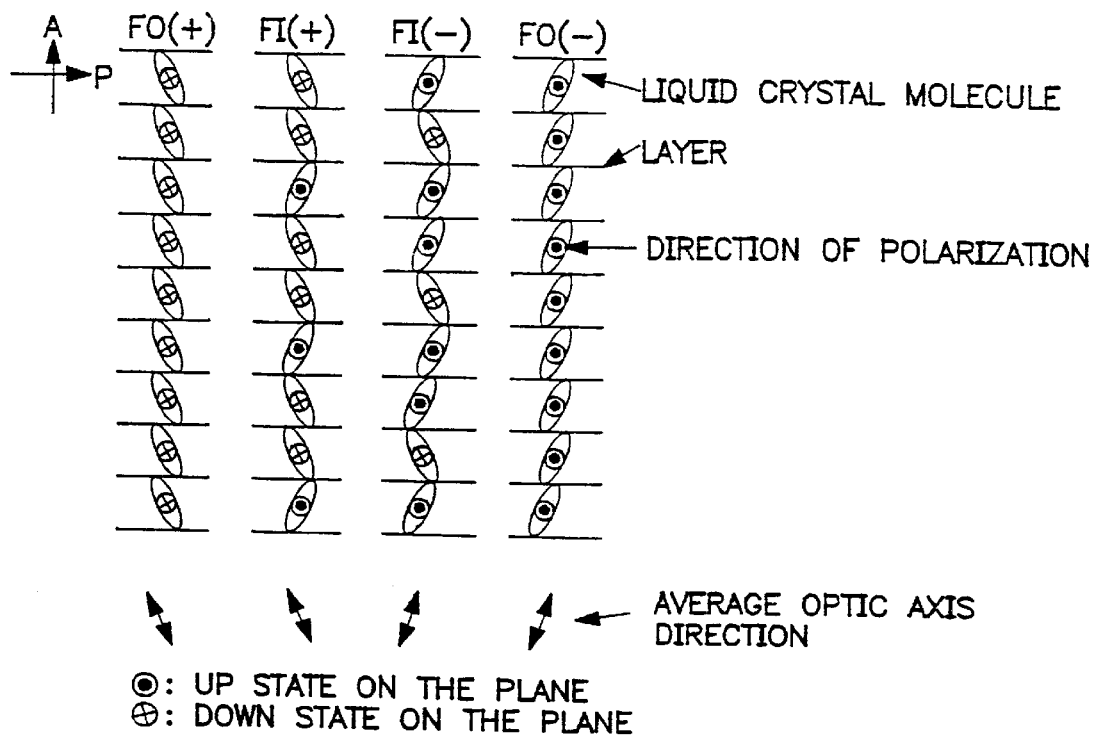
FIG. 1
Figure 2:
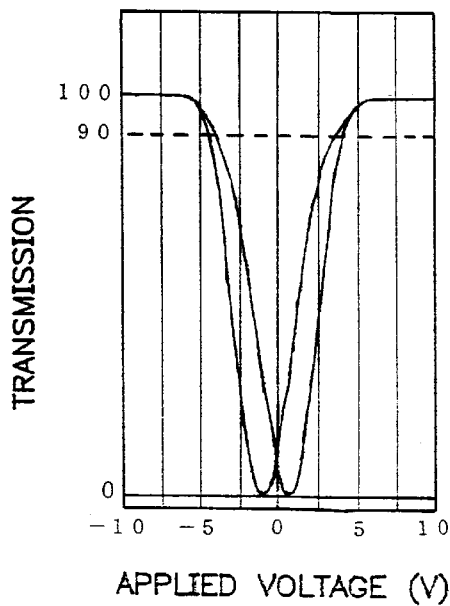

FIG. 1 shows molecular arrangement states of a ferrielectric phase, and FIG. 2 shows an optical response of a ferrielectric phase to a triangular wave voltage, for explaining a ferrielectric phase.

A ferrielectric phase has a molecular arrangement states of FI(+) (a case where an applied voltage is positive) or a molecular arrangement states of FI(−) (a case where an applied voltage is negative) as shown in FIG. 1. In a state free of an electric field, FI(+) and FI(−) are equivalent and are therefore co-present.

Therefore, average optic axes are in the direction of a layer normal, and a dark state is formed under the condition of a polarizer shown in FIG. 1. This state corresponds to a portion where a transmitted light intensity of 0 at a voltage of 0 in FIG. 2.

Further, each of FI(+) and FI(−) has spontaneous polarization as is apparent from the molecular arrangement states. However, each spontaneous polarization is canceled by other in a state in which these are co-present and consequently, an average spontaneous polarization is zero. This shows that, like an anti-ferroelectric phase, a ferrielectric phase is free from an image sticking phenomenon observed in a ferroelectric phase.

As an electric field is applied in a ferrielectric phase, a region (domain) having an extinguished position appears first at a voltage lower than a voltage at which a ferroelectric state is reached. This shows that the above domain has an optic axis in the direction that tilts from the direction of layer normal although the tilt is not so large as that in a ferroelectric state.

The above intermediate state is considered to be FI(+) or FI(−). In this case, not a continuous change in transmitted light intensity but a stepwise transmitted light intensity ought to be observed between a voltage of 0 V and a voltage of 4 V in FIG. 2. In FIG. 2, however, a continuous transmitted light intensity was observed. That is presumably because the threshold voltage of FI(+)→FO(+) or FI(−)→FO(−1) is not distinct.

As far as the liquid crystal compound of the present invention is concerned, a liquid crystal phase which always shows the above intermediate state is called a ferrielectric phase, and a liquid crystal compound or a liquid crystal composition of which the ferrielectric phase is the broadest in its phase sequence is called a ferrielectric liquid crystal compound.

When the applied voltage is further increased, the ferrielectric phase causes a phase transition to a ferroelectric phase FO(+) or FO(−) that is a stabilized state, depending upon a direction of the electric field. That is, in FIG. 2, a phase in which the intensity of transmitted light is brought into a saturated state (flat portions on left and right sides) is FO(+) or FO(−).

It is seen in FIG. 1 that the above ferroelectric state FO(+) or FO(−) has a greater spontaneous polarization than the ferrielectric state FI(+) or FI(−).

As described above, in the ferrielectric phase, the co-presence state of FI(+) and FI(−) can be used as dark, and the ferroelectric states FO(+) and FO(−), as light.

A conventional ferroelectric phase provides a switching between FO(+) and FO(−), while the ferrielectric phase has a great characteristic feature that it permits switching among four states of FO(+), FI(+), FI(−) and FO(−).

However, the display principle thereof uses birefringence of a liquid crystal, and a display device having a decreased viewing angle dependency can be produced.

As shown in FIG. 2, generally, a ferrielectric phase has a tendency that a difference between the voltage required for change from a ferrielectric state to a ferroelectric state and the voltage required for change from a ferroelectric state to a ferrielectric state is small, that is, the width of its hysteresis is very narrow. It characteristically shows an optical response having a V-letter-shape and has properties suitable for an active matrix driving (AM driving) and a display with a gray scale in AM driving.

Further, in the ferrielectric phase, the voltage (to be referred to as "phase transition voltage" hereinafter) required for a phase change between a ferrielectric state and a ferroelectric state tends to be very small as compared with that of an anti-ferroelectric phase, and it can be therefore said that the ferrielectric phase is suitable for AM driving.

However, the number of ferrielectric liquid crystal compounds that have been synthesized so far is very small, and when application to an AM driving device is taken into account, few ferrielectric liquid crystal that have been already known are satisfactory in respect of hysteresis and a voltage in the phase transition.

Further, in the active matrix driving device, it is an essential problem in practical driving how large or small the spontaneous polarization of the ferrielectric liquid crystal is.

J. Funfscilling et al. show that in the AM driving, the degree of the voltage required for driving a liquid crystal having spontaneous polarization is in proportion to the spontaneous polarization (Jpn. J. Appl. Phy. Vol. 33, pp 4950 (1994)). It is desirable from the aspect of driving voltage, therefore, that the spontaneous polarization is as small as possible.

On the other hand, it is thought that the speed ("to be referred to as "response speed" hereinafter) in the phase transition from a ferrielectric state to a ferroelectric state is largely in proportion to the spontaneous polarization.

It is therefore very advantageous in practice if there can be provided a ferrielectric liquid crystal having a small spontaneous polarization and having a high response speed.

Means to Solve the Problems

That is, according to the present invention, there is provided a fluorine-substituted compound of the following general formula (1) or (2), and there is also provided a ferrielectric liquid crystal composition prepared by incorporating the above fluorine-substituted compound into a ferrielectric liquid crystal of at least one or a mixture of two or more compounds selected from compounds of the following general formula (3),

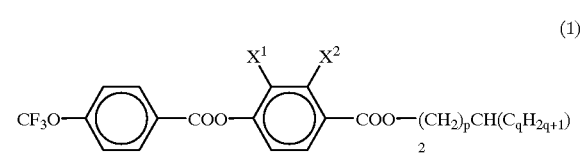

(1)

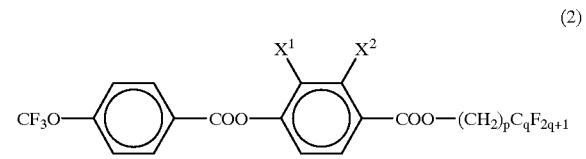

(2)

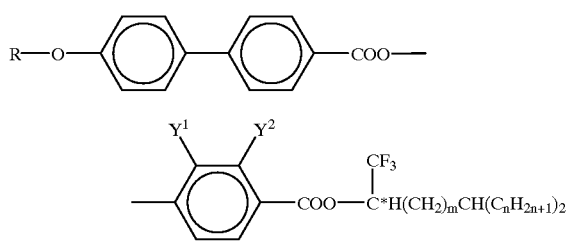

wherein, in the formula (1), each of $X^1$ and $X^2$ is a hydrogen atom, or one of them is a hydrogen atom and the other is a fluorine atom, p is an integer of 0 to 3 and q is an integer of 1 to 3, in the formula (2), each of $X^1$ and $X^2$ is a hydrogen atom, or one of them is a hydrogen atom and the other is a fluorine atom, p is an integer of 1 to 3 and q is an integer of 1 to 3, and in the formula (3), R is an integer of a linear alkyl group having 6 to 12 carbon atoms, each of $Y^1$ and $Y^2$ is a hydrogen atom, or one of them is a hydrogen atom and the other is a fluorine atom, m is an integer of 0 to 4, and n is an integer of 1 to 4.

In the present invention, a compound of the above general formula (1) in which both $X^1$ and $X^2$ are hydrogen atoms, p is 1 and q is 2 exhibits excellent characteristics as a property improving agent. Further, in the general formula (2), preferably, $X^1$ and $X^2$ are hydrogen atoms, p is 1 and q is 1.

When there is used a ferrielectric liquid crystal of at least one or a mixture of two or more compounds from the compounds of the above general formula (3) in which the number of carbon atoms of R is 9, $Y^1$ is a hydrogen atom and $Y^2$ is a fluorine atom, there is provided a ferrielectric liquid crystal composition having excellent performances.

Further, the content of the fluorine-substituted compound of the general formula (1) or (2) in the composition is preferably 1 to 50 mol %, more preferably 10 to 40 mol %, particularly preferably 10 to 30 mol %. Preferably, the transition temperature of ferrielectric phase of the ferrielectric liquid crystal composition on the high-temperature side is at least 40° C., the transition temperature thereof on the low-temperature side is 0° C. or lower, and the composition has a smectic A phase on a temperature side higher than the temperature of the above ferrielectric phase.

The ferrielectric liquid crystal composition provided by the present invention can give an active matrix liquid crystal display device by interposing it between substrates on which non-linear active devices such as thin film transistors or diodes are provided for individual pixels. In the active matrix liquid crystal display device, switching can be performed among two ferrielectric states, two ferroelectric states and intermediate states between them on the basis of voltages, and full color displaying can be attained at a high response speed.

The ferrielectric liquid crystal in the present invention can be easily produced according to Japanese Patent Application No. 8-91235 invented by the same inventors in the present invention. The method for the production thereof will be outlined as follows with regard to a compound of the formula (3) in which R=9, $Y^1$=H, $Y^2$=F, m=2 and n=2.

AcO—Ph(3F)—COOH+SOCl$_2$→AcO—Ph(3F)—COCl (1)

(1)+CF$_3$C*H(OH)(CH$_2$)$_2$CH(C$_2$H$_5$)$_2$→$_{AcO—Ph}$(3F)—COO—C*H(CF$_3$)(CH$_2$)$_2$CH(C$_2$H$_5$)$_2$ (2)

(2)+(Ph—CH$_2$NH$_2$)→HO—Ph(3F)—COO—C*H(CF$_3$)(CH$_2$)$_2$CH(C$_2$H$_5$)$_2$ (3)

C$_9$H$_{19}$—O—Ph—Ph—COOH+SOCl$_2$→C$_9$H$_{19}$—O—Ph—Ph—COCl (4)

(3)+(4)→Ferrielectric liquid crystal as an end product. (5)

In the above formulae, AcO is an acetyl group, Ph is a 1,4-phenylene group, Ph(3F) is a 1,4-phenylene group in which fluorine is substituted on the 3-position, and C* is an asymmetric carbon.

The above production method will be briefly explained below.

(1) shows the chlorination of p-acetoxybenzoic acid in which fluorine is substituted on the 3-position with thionyl chloride.

(2) shows the formation of an ester by a reaction between a chloride (1) and an optically active alcohol.

(3) shows the deacetylation of the ester (2).

(4) shows the chlorination of 4'-alkyloxybiphenyl-4-carboxylic acid.

(5) shows the production of a liquid crystal by a reaction between a phenol (3) and the chloride (4).

EFFECT OF THE INVENTION

The present invention provides a novel fluorine compound and a ferrielectric liquid crystal composition containing the same. The novel ferrielectric liquid crystal composition provided by the present invention has small spontaneous polarization and has excellent response characteristics so that a ferrielectric liquid crystal display device having high display qualities can be materialized.

EXAMPLES

The present invention will be explained more in detail with reference to Examples hereinafter, while the present invention shall not be limited thereto.

Example 1

(formula (1): $X^1$=H, $X^2$=F, p=1, q=2) (E1)

Preparation of 3-fluoro-4-(2-ethylbutyloxy)carbonylphenyl-4'-trifluoromethoxybenzoate (1) Preparation of 2-fluoro-4-acetoxy-1-(2-ethylbutyloxy)carbonylbenzene Thionyl chlorine in an amount of 60 ml (milliliter) was added to 11.9 g (0.06 mol) of 2-fluoro-4-acetoxybenzoic acid, and the mixture was allowed to react under reflux for 7 hours. Then, excess thionyl chloride was distilled off, and then 10 ml of pyridine and 3.7 g (0.0402 mol) of 2-ethyl-1-butanol were dropwise added.

After the addition, the mixture was stirred at room temperature for 1 day and then diluted with 200 ml of ether, and an organic layer was washed consecutively with diluted hydrochloric acid, with a 1N sodium hydroxide aqueous solution and with water and dried over magnesium sulfate. The solvent was distilled off and the residue was purified with a silica gel column chromatograph using hexane/ethyl acetate as a solvent, to give an end product in the yield of 90%.

(2) Preparation of 2-fluoro-4-hydroxy-1-(2-ethylbutyloxy)carbonylbenzene 9.3 Grams (0.036 mol) of the compound prepared in the above (1) was dissolved in 250 ml of ethanol, and 7.7 g (0.0772 mol) of benzylamine was dropwise added. Further, the mixture was stirred at room temperature for 1 day, then diluted with 300 ml of ether, consecutively washed with diluted hydrochloric acid and with water, and dried over magnesium sulfate. The solvent was distilled off, and the residue was purified for isolation with a silica gel column chromatograph to give an end product in the yield of 95%.

(3) Preparation of 3-fluoro-4-(2-ethylbutyloxy) carbonylphenyl-4'-trifluoromethoxybenzoate To 6.4 g (0.031 mol) of commercially available p-trifluoromethoxybenzoic acid was added 15 ml of thionyl chloride, and the mixture was refluxed under heat for 5 hours. Excess thionyl chloride was distilled off, then, 2 ml of pyridine and 2.12 mmol of the compound prepared in the above (2) were added, and the mixture was allowed to react at room temperature for 10 hours. After completion of the reaction, the reaction mixture was diluted with 300 ml of ether and consecutively washed with diluted hydrochloric acid, with a 1N sodium carbonate aqueous solution and with water, and an organic layer was dried over magnesium sulfate.

Then, the solvent was distilled off, and an end product was isolated by silica gel column chromatography to give the end product in the yield of 87%.

The following (E1) and (E2) show formulae of the obtained fluorine compounds, and Table 1 shows NMR-spectra.

Example 2

(formula (2): $X^1$=H, $X^2$=H, p=1, q=1   (E2))

Preparation of 4-(2,2,2-trifluoroethoxy)-carbonylphenyl-4'-trifluoromethoxybenzoate (1) Preparation of 4-acetoxy-1-(2,2,2-trifluoroethoxy)carbonylbenzene Thionyl chloride in an amount of 60 ml (milliliter) was added to 10.8 g (0.06 mol) of 4-acetoxybenzoic acid, and the mixture was allowed to react under reflux for 7 hours. Then, excess thionyl chloride was distilled off, and then 10 ml of pyridine and 4.0 g (0.0402 mol) of 2,2,2-trifluoroethanol were dropwise added. After the addition, the mixture was stirred at room temperature for 1 day and then diluted with 200 ml of ether, and an organic layer was washed consecutively with diluted hydrochloric acid, with a 1N sodium hydroxide aqueous solution and with water and dried over magnesium sulfate. The solvent was distilled off and the residue was purified with a silica gel column chromatograph using hexane/ethyl acetate as a solvent, to give an end product in the yield of 90%.

(2) Preparation of 4-hydroxy-1-(2,2,2-trifluoroethoxy) carbonylbenzene 9.4 Grams (0.036 mol) of the compound prepared in the above (1) was dissolved in 250 ml of ethanol, and 7.7 g (0.0772 mol) of benzylamine was dropwise added. Further, the mixture was stirred at room temperature for 1 day, then diluted with 300 ml of ether, consecutively washed with diluted hydrochloric acid and with water, and dried over magnesium sulfate. The solvent was distilled off, and the residue was purified for isolation with a silica gel column chromatograph to give an end product in the yield of 98%.

(3) Preparation of 4-(2,2,2-trifluoroethoxy)-carbonylphenyl-4'-trifluoromethoxybenzoate To 6.4 g (0.031 mol) of commercially available p-trifluoromethoxybenzoic acid was added 15 ml of thionyl chloride, and the mixture was refluxed under heat for 5 hours. Excess thionyl chloride was distilled off, then, 2 ml of pyridine and 2.12 mmol of the compound prepared in the above (2) were added, and the mixture was allowed to react at room temperature for 10 hours. After completion of the reaction, the reaction mixture was diluted with 300 ml of ether and consecutively washed with diluted hydrochloric acid, with a 1N sodium carbonate aqueous solution and with water, and an organic layer was dried over magnesium sulfate.

Then, the solvent was distilled off, and an end product was isolated by silica gel column chromatography to give the end product in the yield of 87%.

The following (E1) and (E2) show formulae of the obtained fluorine compounds, and Table 1 shows NMR-spectra.

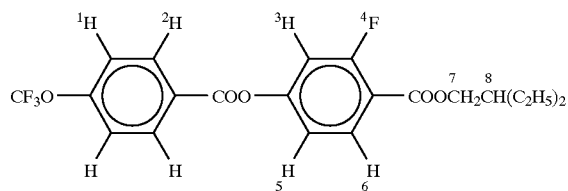

(E1)

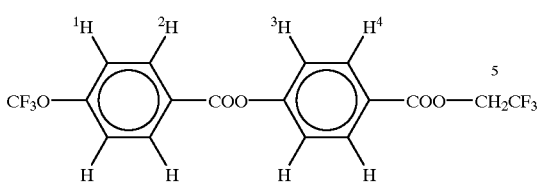

(E2)

TABLE 1

| Proton No. | 1 | 2 | 3 | 4 | 5 | 6 | 7 | 8 |
|---|---|---|---|---|---|---|---|---|
| Example 1 (E1) | 7.4 | 8.2 | 7.1 | — | 7.1 | 8.0 | 4.3 | 1.6 |
| Example 2 (E2) | 7.4 | 8.2 | 7.4 | 8.2 | 4.7 | — | — | — |

Example 3

A compound (1A) which was obtained in Example 1 and correspond to a compound of the general formula (1) was mixed with a mixture of the following ferrielectric liquid crystals (3A, 3B) corresponding to compounds of the general formula (3) in the following molar ratio, to prepare a ferrielectric liquid crystal composition.

1A: $CF_3O$—Ph—COO—Ph(3F)—COO—$CH_2CH(C_2H_5)_2$ 35 mol %

3A: $C_9H_{19}O$—PhPh—COO—Ph(3F)—COO—$C^*H(CF_3)$ $(CH_2)_2CH(C_2H_5)_2$ 26 mol %

3B: $C_9H_{19}O$—PhPh—COO—Ph(3F)—COO—$C^*H(CF_3)$ $(CH_2)_2CH(CH_3)_2$ 39 mol %

The above-obtained ferrielectric liquid crystal composition and the ferrielectric liquid crystals (2A, 2B) and the fluorine-substituted compound (1A) that were used were measured for liquid crystal phase sequences, phase transition voltages, response speeds and spontaneous polarizations, and Table 2 shows the results.

Liquid crystal phases were identified by texture observation, conoscopic image observation and DSC (differential scanning calorimeter) measurement. The observation of a conoscopic image is an effective means for identifying a ferrielectric phase. The conoscopic image observation was conducted according to a literature (J. Appl. Phys. 31, 793 (1992)).

Further, optical responses were measured. Cells were prepared by the following procedure.

A pair of glass plates with insulating film ($SiO_2$, film thickness; 50 nm) and ITO electrodes were coated with polyimide (film thickness, about 80 nm), and one of a pair of the glass plates was rubbed.

A pair of the glass plates were attached to each other through a spacer having a particle diameter of 1.6 μm to form a test cell. The cell had a thickness of 2.1 μm.

The composition was heated until the liquid crystals showed an isotropic phase, and then the liquid crystals were injected into the test cell by capillarity. Thereafter, the cell was gradually cooled at a rate of 1° C./minute to align the liquid crystals in parallel.

In defining light transmittance, the lowest intensity of transmitted light was defined to be 0% of light transmittance, and the highest intensity of transmitted light was defined to be 100% of light transmittance. The phase transition voltage was defined to be a voltage found at a light transmittance of 90%.

A triangular wave voltage of ±10 V, 50 mHz was applied to the test cell at 30° C., and a voltage (phase transition voltage) in the transition from a ferrielectric phase to a ferroelectric phase was determined.

The response speed was defined to be a time period required for a 90% change of the light transmittance when a step voltage of ±5V, 10 Hz was applied to the test cell at 30° C., and the test cell was measured for a response speed.

Further, the spontaneous polarization was determined by applying a triangular wave voltage of 10 V to the test cell at 50° C. and measuring a polarization inversion current.

Example 4

A ferrielectric liquid crystal composition was prepared in the same manner as in Example 3 except that the fluorine compound (1A) obtained in Example 1 was replaced with the fluorine compound (2A) obtained in Example 2. The composition was similarly measured for physical properties, and Table 2 shows the results.

2A: $CF_3OPhCOOPhCOOCH_2CF_3$ 35 mol %

TABLE 2

| | Phase sequence | Phase transition voltage (V) | Response time (μ second) | Spontaneous polarization (nC/cm$^2$) |
|---|---|---|---|---|
| Example 3 | Cr(< −20)SCγ*(40)SA(73)I | 2.9 | 196 | 36 |
| Example 4 | Cr(< −20)SCγ*(55)SA(83)I | 3 | 129 | 63 |
| Liquid crystal 3A | Cr(26)SCγ*(95)I | 2.4 | 257 | 209 |
| Liquid crystal 3B | Cr(57)SCγ*(114)I | 1.3*1 | 13*1 | 200 |
| Compound 1A | Liquid | | | |
| Compound 2A | Cr(70)I | | | |

In Table, phase transition voltage (*1) and response time (*1) of liquid crystal 3B were values measured at 60° C.

Further, parenthesized values in the column of "Phase sequence" show phase transition temperatures (° C.), Cr is a crystal phase, SCγ* is a chiral smectic Cγ phase (ferrielectric phase), and I is an isotropic phase.

What is claimed is:

1. A fluorine-substituted compound of the following general formula (1) or (2),

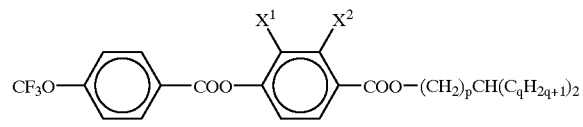

(1)

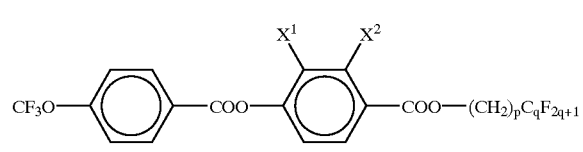

(2)

wherein, in the formula (1), each of $X^1$ and $X^2$ is a hydrogen atom, or one of them is a hydrogen atom and the other is a fluorine atom, p is an integer of 0 to 3 and q is an integer of 1 to 3, and in the formula (2), each of $X^1$ and $x^2$ is a hydrogen atom, or one of them is a hydrogen atom and the other is a fluorine atom, p is an integer of 1 to 3 and q is an integer of 1 to 3.

2. The fluorine-substituted compound of claim 1, wherein, in the general formula (1) or (2), $X^1$ and $X^2$ are hydrogen atoms together.

3. The fluorine-substituted compound of claim 1 or claim 2, which is the compound of general formula (1), wherein p is 1 and q is 2.

4. The fluorine-substituted compound of claim 1 or claim 2, which is the compound of general formula (2), wherein p is 1 and q is 1.

5. A ferrielectric liquid crystal composition comprising a fluorine-substituted compound of the following general formula (1) or (2) incorporated into a ferrielectric liquid crystal of at least one selected from ferrielectric liquid crystal compounds of the following general formula (3) or a mixture of two or more selected from the compounds of the following general formula (3),

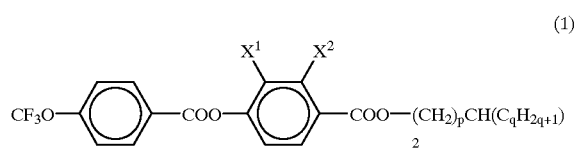

(1)

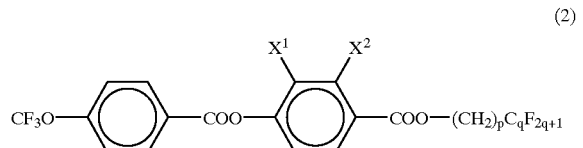

(2)

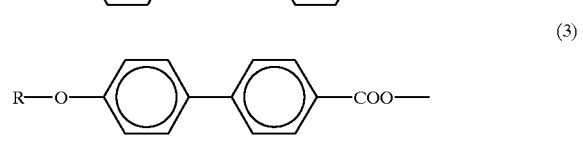

(3)

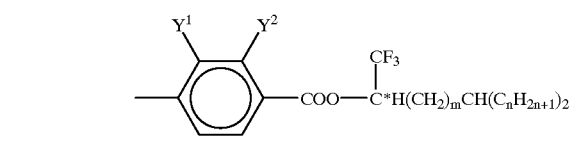

wherein, in the formula (1), each of $X^1$ and $X^2$ is a hydrogen atom, or one of them is a hydrogen atom and the other is a fluorine atom, p is an integer of 0 to 3 and q is an integer of 1 to 3, in the formula (2), each of $X^1$ and $X^2$ is a hydrogen atom, or one of them is a hydrogen atom and the other is a fluorine atom, p is an integer of 1 to 3 and q is an integer of 1 to 3, and in the formula (3), R is a linear alkyl group having 6 to 12 carbon atoms, each of $Y^1$ and $Y^2$ is a hydrogen atom, or one of them is a hydrogen atom and the other is a fluorine atom, m is an integer of 0 to 4, and n is an integer of 1 to 4.

6. The ferrielectric liquid crystal composition of claim 5, wherein, in the general formula (3), R is a linear alkyl group having 9 carbon atoms.

7. The ferrielectric liquid crystal composition of claim 5, wherein, in the general formula (3), $Y^1$ is a hydrogen atom and $Y^2$ is a fluorine atom.

8. The ferrielectric liquid crystal composition of claim 5, wherein the content of the fluorine-substituted compound of the general formula (1) or (2) in the composition is 1 to 50 mol %.

9. The ferrielectric liquid crystal composition of claim 5, which has a transition temperature of a ferrielectric phase at 40° C. or higher on a high-temperature side and a transition temperature thereof at 0° C. or lower on a low-temperature side and which has a smectic A phase on a temperature side higher than the temperature of the above ferrielectric phase.

10. An active-matrix liquid crystal display device, in which the ferrielectric liquid crystal composition of claim 5 is interposed between substrates on which non-linear active devices are provided for individual pixels.

11. The active-matrix liquid crystal display device of claim 10, characterized in that switching is performed among two ferrielectric states, two ferroelectric states and intermediate states between them on the basis of voltage changes.

12. The active-matrix liquid crystal display device according to claim 10, wherein the non-linear active devices comprise thin film transistors.

13. The active-matrix liquid crystal display device according to claim 10, wherein the non-linear active devices comprise diodes.

14. The ferrielectric liquid crystal composition according to claim 5, wherein in the compounds of formula (1) and formula (2), each of $X^1$ and $X^2$ are hydrogen, and in formula (1) p is 1 and q is 2; and in formula (2), p is 1 and q is 1.

15. The ferrielectric liquid crystal composition according to claim 5, wherein the content of the fluorine-substituted compound of formula (1) or formula (2) is from 10 to 40 mol %.

16. The ferrielectric liquid crystal composition according to claim 5, wherein the content of the fluorine-substituted compound of formula (1) or formula (2) is from 10 to 30 mol %.

* * * * *